United States Patent [19]

Gardner, Jr.

[11] Patent Number: 5,188,123
[45] Date of Patent: Feb. 23, 1993

[54] HEARING PROTECTIVE EARPLUG HAVING ALTERNATIVE MODES OF INSERTION

[75] Inventor: Ross Gardner, Jr., Indianapolis, Ind.

[73] Assignee: Cabot Safety Corporation, Southbridge, Mass.

[21] Appl. No.: 819,614

[22] Filed: Jan. 9, 1992

Related U.S. Application Data

[63] Continuation of Ser. No. 570,348, Aug. 20, 1990, abandoned.

[51] Int. Cl.$^5$ ............................................. A61F 11/00
[52] U.S. Cl. ................................................... 128/864
[58] Field of Search ................................ 128/864–867

[56] References Cited

U.S. PATENT DOCUMENTS

| Re. 29,487 | 12/1977 | Gardner | 128/864 |
| 2,538,339 | 1/1951 | Thomas | 128/151 |
| 3,881,570 | 5/1975 | Lewis | 128/864 |
| 4,122,841 | 10/1978 | Rock | 128/864 |
| 4,158,087 | 6/1979 | Wood | 521/137 |
| 4,253,452 | 3/1981 | Powers | 128/864 |
| 4,314,553 | 2/1982 | Westerdal | 128/152 |
| 4,774,938 | 10/1988 | Leight | 128/864 |
| 4,867,149 | 9/1989 | Falco | 128/864 |

FOREIGN PATENT DOCUMENTS

| 2325823 | 12/1974 | Fed. Rep. of Germany . |
| 733542 | 7/1955 | United Kingdom . |

Primary Examiner—Robert A. Hafer
Assistant Examiner—Michael Brown
Attorney, Agent, or Firm—Michelle B. Lando

[57] ABSTRACT

A hearing protective earplug which permits alternative push-in and roll-down modes of insertion. The earplug includes a soft, smoothly contoured, resilient, homogeneous viscoelastic polymeric foam main body element having a manipulable stem axially embedded therein and extending outwardly from its base.

16 Claims, 1 Drawing Sheet

HEARING PROTECTIVE EARPLUG HAVING ALTERNATIVE MODES OF INSERTION

This is a continuation of copending application Ser. No. 07/570,348 filed on Aug. 20, 1990, now abandoned.

BACKGROUND OF THE INVENTION

The present invention relates generally to hearing protective earplugs and is more particularly concerned with premolded, polymeric foam earplugs of the push-in type.

Premolded polymeric foam earplugs composed of resilient polymer foam materials such as foam rubber, polyurethane or plasticized polyvinylchloride are well known in the art. For instance, in United Kingdom Patent No. 733,542, to Hultgren, there is disclosed a push-in type earplug comprising a soft, elastic, bullet-shaped spongy body element having a stiff axially oriented stem by which to facilitate insertion and removal of the spongy body element into and from the ear canal. Hultgren also discloses the possibility of controlling the acoustic attenuation properties of his plug by varying the pore size and density of the spongy body element. A major problem generally incurred with premolded earplugs of the prior art resides in the anatomical fact that the human ear canal is quite variable in size and geometry and, as a result, a single size of a premolded prior art earplug has not been found capable of accommodating the broad range of human ear canal sizes. Thus, premolded earplugs are generally produced in several sizes which, of course, increases the complexity and cost of manufacture and is bothersome throughout the distribution chain in terms of expense and complexity of purchasing and inventory control. As in the case of many other prior art premolded plugs, the earplugs of Hultgren are also said to be produced in two or three sizes. In addition, in order to assure good attenuation performance, the Hultgren plugs, as in the case of any earplug which is provided in several sizes, should be fitted to the individual wearer by a skilled hearing protection specialist. Unlike my present invention, the bullet-shaped spongy body element of the earplug disclosed by Hultgren is not possessed of viscoelastic recovery properties.

U.S. Pat. No. 2,438,339, issued to M. J. Thomas, discloses a frusto-conically shaped earplug of the push-in type having an elongated stiff cylindrical core composed of a material such as hard rubber. This core is surrounded by a frusto-conically shaped body composed of soft expandable and contractible material such as sponge rubber. The embedded stiff core is disclosed to be coextensive with the frusto-conically shaped body; that is to say, it does not extend outside the body element and thus cannot serve as a stem by which to manipulate the plug into and from the ear canal. Rather, the sole function served by the core element in the Thomas invention is that of stiffening of the body element such that the foam body is prevented from excessive lateral bending or distortion during insertion of the plug into the ear canal. In addition, Thomas mentions nothing with respect to the recovery rate or other properties of the body element of her earplug construction.

In West German No. OS 2 325 823, to Envac Establishment, filed on May 22, 1973 and laid open on Dec. 19, 1974, there is disclosed an earplug comprising a spherical polymeric foam body element having an essentially impermeable outer surface and a stiff elongate handle extending therefrom. The foam body element can be composed of such polymeric materials as polyurethane or plasticized polyvinylchloride. As in the Hultgren and Thomas patents discussed above, this opened West German application neither discloses nor suggests a viscoelastic foam body element and the plug construction taught therein is solely of the push-in type.

In my prior U.S. Pat. Nos. 3,811,437 and Re. 29,487 there are taught certain roll down type hearing protective earplugs composed of viscoelastic polymeric foam and having a size and shape adapted to be compressed, inserted into the ear canal and therein allowed to expand to result in a comfortable and complete obturation of the ear canal. Earplugs manufactured in accordance with the aforementioned patents have met with outstanding commercial success in the marketplace due to their features of easy insertability, comfort, excellent attenuation properties and their ability to be produced in a single size while competently fitting almost the entire adult population. Nevertheless, said foam earplugs do possess certain deficiencies which mitigate against their use in certain hearing protective situations. Firstly, the earplugs of my above-identified patents are prepared for insertion by initially rolling them down between thumb and fingers, thereby to compress them to below the sizes of the ear canals into which they are to be inserted. In terms of hygiene, therefore, the user's hands should be at least relatively clean at the time of use. This is not a trivial matter because in many noisy industrial environments there are abrasive materials or harsh chemicals which can become imbedded in the earplug. These contaminants may be present on the workers' hands at the time of use of the plugs and the necessity for first cleansing the hands can be a bothersome requisite in such situations. Additionally, while the preliminary step of rolling the plugs between the fingers is, indeed, a simple physical step, hand disabled users, such as those suffering from arthritis, can find the roll-down step a near or actual impossibility.

OBJECTS OF THE INVENTION

It is a principal object of the invention to provide a new and novel hearing protective earplug construction.

It is still another object of the invention to provide a new and novel earplug construction which may be utilized either as a push-in or roll-down plug.

It is another object of the invention to provide an earplug construction which may be produced in a single size, but which provides easy insertion, wearer comfort and good sound attenuation to substantially the entire adult population.

Other objects and advantages of the invention will in part be obvious and will in part appear hereinafter

SUMMARY OF THE INVENTION

In its broadest aspect the earplug of the invention comprises a resilient polymeric foam body comprising a smoothly contoured, homogeneous and viscoelastic main body element having a rounded nose end. The main body element is of circular or ovoid cross section, the maximum cross sectional dimension thereof at any point along its length being no greater than about 13.73 mm (0.540 inch). An elongate stem is axially embedded in the main body element and extends rearwardly through the base and terminates exterior the base. The main body element of the earplug construction of the invention has a 90% recovery rate, as determined by the test described hereinafter, of between 2 and 120 seconds.

DESCRIPTION OF THE PREFERRED EMBODIMENTS

Figure 1:
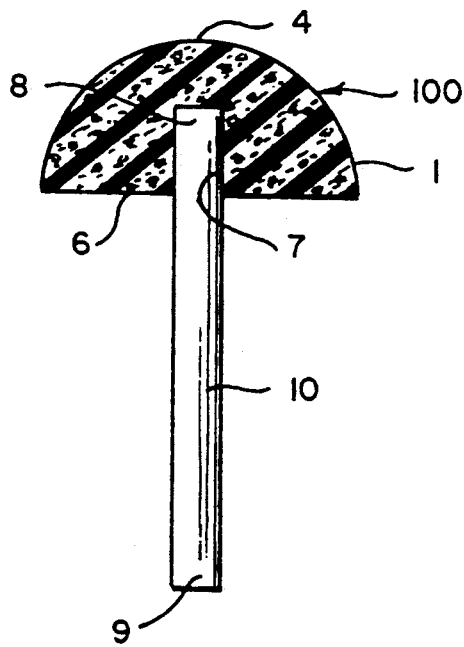
FIG. 1 hereof is a side view, partly in section, of an earplug in accordance with the invention.
Figure 2:
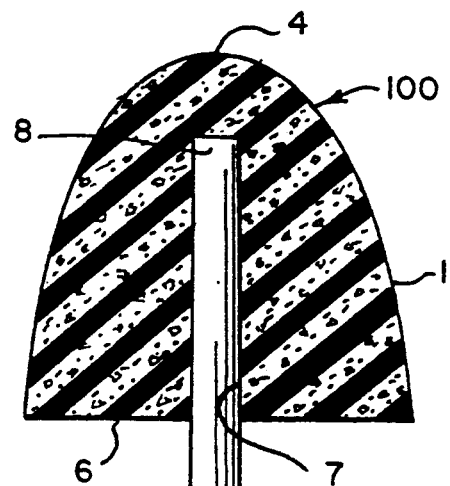
FIG. 2 is a side view, partly in section, of another embodiment of an earplug in accordance with the invention.
Figure 3:
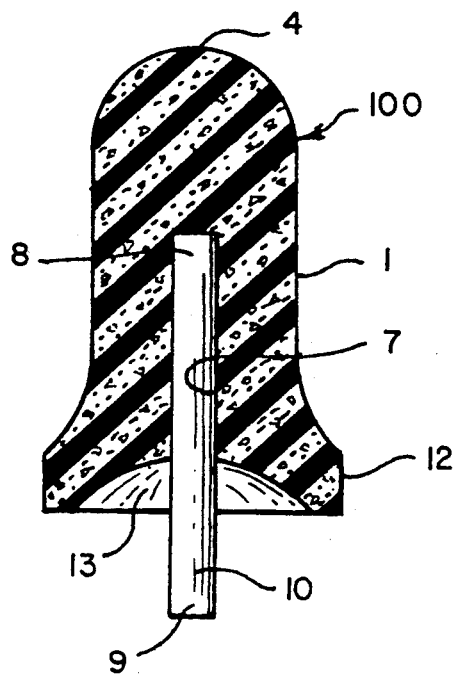
FIG. 3 is a side view, partly in section, of still another embodiment of an earplug in accordance with the invention.

Referring now to FIGS. 1 through 3, wherein like reference numerals refer to like structures, the earplug construction of the invention broadly comprises a soft, resilient polymeric foam body 100 comprising a smoothly contoured, homoegenous, viscoelastic main body element 1 adapted in size and shape to be inserted into the human ear canal in acoustically obturating relationship therewith and an elongate stem 10 extending rearwardly and axially therefrom. While the preferred cross sectional shape of the main body element 1 is circular, it will be appreciated that said cross sectional shape may also be ovoid or elliptical. By the term, "homogeneous", it is meant that the main body element 1 of the body 100 is devoid of lateral projections or internal cavities, such as in the nature of one or more flange elements or substantial cavities therein (other than the stem-receiving recess 7). In order to achieve the essentially universal fit benefit of the invention and depending somewhat upon the density and softness of the polymeric foam of which it is composed and the specific geometry of the foam main body element 1, the maximum cross sectional dimension thereof at any point along its length can be up to about 13.72 mm (0.540 inch).

In the particular embodiment of the invention depicted in FIG. 3, the main body element 1 transitions into a terminal flared end portion 12 lying at the outboard end and which flared end portion 12 has a larger maximum cross sectional dimension than that of the external auditory meatus or opening of the average human ear canal. Where this design consideration is met, the flared end portion 12 functions as a convenient stop means, whereby an appropriate depth of insertion of the main body element 1 into the ear canal is facilitated. Upon insertion of the main body element 1 into the ear canal, using the roll-down or push-in mode of insertion, the terminal flared end portion 12 ultimately butts against the opening of the ear canal, thereby to signal the user that the appropriate insertion depth has been attained. Additionally, upon said butting of the terminal flared end portion 12 against the opening of the ear canal, over-insertion of the main body element 1 is rendered difficult due to the interference provided by said flared end portion 12. While the precise maximum cross sectional dimension for the flared end portion 12 is subject to considerable variation, I have found that a terminal flared end portion 12 of circular cross section and having a diameter of about 19.05 mm (0.75 inch) is usually adequate to serve this beneficial stop means function. The main body element 1 is, for purposes of the invention, defined as that portion of the polymeric foam body 100 which is insertable into the ear canal. Thus, where the earplug of the invention bears the terminal flared end portion 12 embodiment such as shown in FIG. 3, said end portion 12 of the polymeric foam body 100 is not to be construed as part of the main body element 1 and the previously disclosed prohibition against internal cavities in the main body element 1 does not attend said flared end portion 12. For instance, as also shown in FIG. 3, said terminal flared end portion 12 can comprise a shallow concavity 13 whose depth does not intrude into the foam material of construction of the main body element 1.

Stem 10 is an elongate member which may be tubular or solid throughout its cross section and may be uniform or slightly tapered along its length. In the case of a slightly tapered configuration, the larger end will normally be utilized as the end 8 inserted into recess 7 of the foam main body element 1. In any event, the cross sectional dimension of stem 10 at said end 8 should not be so great as to prevent easy insertion of the earplug into ear canals of small size. To this end, I prefer that the maximum cross sectional dimension of the stem 10 at end 8 be within the range of from 3.2 mm (0.125 inch) to 4.0 mm (0.16 inch). The stem 10, of course, can be of any convenient length such that the free end 9 thereof extends beyond the body element 1 and, if utilized, the terminal flared end portion 12, so as to provide a conveniently manipulable insertion and removal member for said foam main body element 1. Thus, the exact length selected for the stem 10 will largely be a matter of choice. Of course, the dimensions, geometry and material of construction employed for the stem 10 are selected such that the stem 10 will be sufficiently stiff as to allow manipulation of the main foam body element 1 into the ear canal whether in the precompressed or uncompressed condition.

Many stem 10 constructions will suggest themselves to those of skill in the art and are suitable. For instance, paper, rubber, cardboard and plastic rod forms of the type often used as medical cotton swab holders are generally of adequately stiff nature and appropriate cross sectional dimension for use in the present earplug construction. So, too, are many known plastic drinking and stirring straws. Whatever the selection of the stem 10 material, however, it is important that the end 8 thereof be attached to the foam main body element 1 with sufficient security as to avoid separation of the stem 10 from the main body element 1 during use. The security of attachment can be achieved in any suitable manner, such as by use of suitable adhesives or by solvent or thermal welding. In a preferred embodiment of the invention, the foam body element 100, including the terminal flared end portion 12, if present, is composed of a molded polyurethane foam and the stem 10 is affixed to the main body element 1 thereof during the molding operation. For example, the stem 10 can be utilized as n insert in the mold for the foam body 100, the end 8 thereof acting as a male mold member for recess 7. As the foam formulation blows and cures in the mold to form the foam body element 100 and the main body element 1 thereof, it additionally bonds firmly and tenaciously to the end 8 of the stem 10.

The smoothly contoured main body element 1 extends rearwardly from a rounded nose or forward end 4. The length of the main body element 1 relative to its maximum cross sectional dimension is subject to considerable variation and is not normally critical. For example, the shape of body element 1 of the earplug shown in FIG. 1 is in the nature of a hemisphere; therefore, its length to diameter ratio is about 0.5 to 1. Contrastingly, in the embodiment of FIG. 2, the body element 1 is shown to be distinctly bullet shaped and has a length to diameter ratio of about 3 to 2. In the embodiment of FIG. 3 the length of the terminal flared end portion 12 is not to be construed as part of the length of the main body element 1. In this case the length of the main body element 1 is taken from the nose end thereof to the point whereat transition thereof into the terminal flared end portion 12 begins. Thus, the length to diameter ratio in the embodiment shown in FIG. 3 is similar to that of the embodiment of FIG. 2, in other words, about 3 to 2.

The relative hardness value of a small ware composed of soft resilient polymeric foam is generally difficult to measure with precision by the Shore 00 Durometer technique. However, with the sole intention of providing a general guideline and with no intention whatsoever of limiting the invention, I have so far found that instantaneous Shore 00 Durometer values of acceptable foams for use as the body element 1 in the present invention appear to be no greater than about 60 Durometer units and have usually been found to reside within the range of from about 20 to about 45 Shore 00 Durometer units. By "instantaneous" value, it is meant that the reading of the Durometer is taken immediately after application of the indentor foot load to the sample and without affording the foam sample time to substantially creep or relax under the load of the indentor foot subsequent to its application.

In general, I prefer that the apparent density of the viscoelastic polymeric foam material of construction of the main body element 1 be no greater than about 0.32 g/cm$^3$ (20 lbs/ft$^3$) and, even more preferably, no greater than about 0.24 g/cm$^3$ (15 lbs/ft$^3$). The apparent density of the main body element 1 can be determined by taking appropriate dimensional measurements from which the volume thereof is calculated, ascertaining its weight and then calculating the apparent density from the thusly obtained volume and weight values. Where the overall body element comprises the terminal flared end portion 12 embodiment, the complexity of the dimensional measurements, volume calculation and density calculation can be markedly reduced simply by cutting off said end portion 12 prior to taking the dimensional and weight measurements of the main body element 1 referred to above.

The resilience of the viscoelastic polymeric foam material of construction of the body element 1 is sufficient as to ensure substantially complete recovery of the original shape and size of said body element when temporarily deformed and released in free space. In addition, in order that the benefit of alternative modes of insertion of the plug be realized, it is important that the polymeric foam employed for the construction of the body element 1 be viscoelastic in nature, in other words that it recover completely, but relatively slowly, when a deforming stress is removed therefrom. Such foams are said to exhibit viscoelastic, as opposed to elastic, behavior. When such viscoelastic foams are employed in the construction of the main body element 1 there results an earplug construction which can be utilized either as a push-in or a roll down type earplug. In the push-in mode, the main body element 1 composed of a viscoelastic polymeric foam can simply be forced into the ear canal by suitable manipulation of the stem 10. However, should the user desire it or should the ear canals of the user be exceptionally small or tortuous, thereby rendering the push-in mode of operation difficult, uncomfortable or undesirable, the user can then use an alternate method of insertion in a manner akin to that described in my U.S. Pat. Re. No. 29,487. Thus, the viscoelastic foam main body element 1 of the invention can be simultaneously rolled and pressed axially between thumb and fingers so as to compress same to below the cross section of the ear canal into which it is to be inserted. Then, arising from the viscoelastic or slow recovery behavior thereof, the user is afforded sufficient time to insert the recovering main body element 1 into the ear canal by suitable manipulation of the stem 10 before recovery of the body element 1 occurs to the extent of interference thereof with the enclosing ear canal wall.

A simple test for recovery rate is to provide a glass or clear plastic tube having an internal diameter 90% of the maximum diameter of the main body element 1 of the earplug under consideration. If the overall body element under consideration also includes the flared terminal end portion 12 embodiment, such as shown in FIG. 3, said flared terminal end portion 12 is first cut off from the test specimens prior to testing of the remaining main body elements 1 thereof. The main body element 1 of the earplug is then rolled down tightly and lengthwise between thumb and fingers for about 30 seconds, released and immediately thereafter inserted into the tube by manipulation of the stem element. At the instant of release of the body element into the tube a stopwatch is started, the tube turned upright over a suitable support surface (such as a table top) and the tube cycled vertically close to and over the support surface at a cyclic rate of approximately 2/second and at an amplitude of approximately 6.35 mm (0.25 inch). The cycling is undertaken such that the free end 9 thereof remains in continuous contact with the support surface until such time as the recovering main body element 1 makes sufficient contact with the enclosed tube as to ride along with said tube during its vertical motion as opposed to sliding freely therewithin. The time for this to occur is noted and is taken as the 90% recovery time. The test procedure is carried out on at least three and preferably at least five sample earplugs of the candidate design and foam formulation in order to establish statistical significance and the results then averaged to provide an average 90% recovery time for the lot under test. Using this procedure, the preferred viscoelastic polymeric foam main body element 1 of the present invention will have an average 90% recovery time of between about 10 to about 60 seconds.

There are many resilient polymeric foam compositions capable of meeting the viscoelastic or slow recovery property requirement of the invention. For instance, many of the externally and internally plasticized polymer foams disclosed in my U.S. Pat. No. Re. 29,487 are generally suitable for use as a material of construction of the main body element 1. So, too, are many of the polyurethane foam compositions disclosed in U.S. Pat. No. 4,158,087, to Louis Leonard Wood, Jun. 12, 1979, entitled, "Urethane Foams Having Low Resiliency". The disclosure of each of the foregoing patents is incorporated herein, in its entirety, by reference.

Polyurethane foam compositions are generally preferred for the body element 1 due to their formulation flexibility, easy molding characteristics and economics. Of these, polyether polyurethane foams are even further preferred due to the generally soft surface "hand" or feel of resilient foam wares produced therewith. The polyether polyurethane foam compositions based on polyurethane prepolymers blended with acrylic latex modifiers in accordance with the above-mentioned Wood patent have been found to be useful in the practice of the invention. Such polyether polyurethane prepolymers are currently available from W. R. Grace Company under the "HYPOL" brand name. Suitable acrylic latex modifiers are available from Union Carbide Corporation under the "UCAR" brand name.

There follows an illustrative, non-limiting example.

EXAMPLE

Ear plugs in accordance with FIG. 1 hereof are produced by molding the foam body elements 1 thereof in a multicavity aluminum mold using a polyether polyurethane foam precursor composition containing a self-crosslinking, acrylic latex modifier. The mold comprises a closure plate having an aperture overlying the center of each body element 1 cavity and through which aperture there is received a stem element 10. Upon injection of the polyetherpolyurethane precursor charges into the respective mold cavities the cover is placed over the mold, thereby bringing the end 8 of each stem element captured in the mold cover apertures to a distance of 1.6 mm (0.054 inch) from the nose end of the mold cavity. The polyetherpolyurethane precursor charge in each cavity blows and partially cures in the closed cavity, the curing and blowing charge thereby filling the cavity, forming the body element 1 and recess 7 and, at the same time, bonding the end 8 of the stem 10 to the polyurethane material of the recess 7. The filling and curing of the mold cavities is undertaken at ambient temperature and, after 10 minutes in the closed mold, the closure plate is removed and the finished earplug wares removed, placed in a fabric bag and dried in a clothes dryer set at the "Medium" cycle in order to remove excess water from the formed wares and to complete the curing of the body elements 1. The particular polyether polyurethane foam precursor formulation employed was as follows:

| Ingredient | Parts by Weight |
|---|---|
| HYPOL 2002, polyether polyurethane prepolymer | 100 |
| UCAR 154, self cross-linking acrylic resin latex | 79.2 |
| Water containing 8.8 wt. percent PLURONIC F68 surfactant (BASF Wyandotte) | 19.8 |
| Sun Yellow YFD, a yellow colorant manufactured by Sun Chemical Company | 1.0 |
| The stem 10 elements were composed of a rolled paper rod stock having a uniform diameter of 4.0 mm (0.156 inch) and a length of 28.7 mm (1.130 inch). | |
| The resulting cured earplugs in accordance with FIG. 1 hereof had the following dimensions: | |
| Length of body element 1 | 6.7 mm (0.262 inch) |
| Maximum diameter of body element 1, taken at base 6 | 13.0 mm (0.510 inch) |
| Exterior shape of body element 1 | hemispherical |

The density of the main foam body element 1 was determined by direct dimensional and weight measurement thereof. The main foam body element 1 was conditioned at room temperature and 50% relative humidity for at least about 24 hours. After carefully separating the stem 10 therefrom, the body element 1 was then weighed on an analytical balance capable of resolving 0.0001 gm. Dimensional measurements thereof were taken using an optical comparator or microscope at a magnification of at least 10×. In the particular embodiment hereof, referring to FIG. 1, the volume of the main foam body element 1 was calculated by first determining the overall volume of the hemispherical body and subtracting from this volume the calculated volume of the cylindrical recess 7. Using this protocol, the density of the main foam body element 1 was found to be 0.216 g/cm$^3$ (13.45 lbs/ft$^3$).

The foam main body element 1 was subjected to Shore 00 Durometer analysis and found to have a Durometer value of about 30.

The average 90% recovery rate of the earplugs was determined as disclosed hereinbefore, utilizing as a gauge a cylindrical glass tube having an internal diameter of 11.7 mm (0.459 inch). Said average 90% recovery rate was determined to be 15.4 seconds.

Several human subjects, having widely varying ear canal sizes and geometries, utilized the earplugs of this example in noisy industrial environments. All subjects reported that the earplugs were easy to use, whether by the push-in or roll-down modes of insertion, were comfortable throughout insertion, wearing and removal and provided adequate attenuation for their needs.

While I have described and shown certain present preferred embodiments of the invention, it is to be distinctly understood that the invention is not limited thereto, but may be variously embodied within the scope of the following claims.

What is claimed is:

1. A hearing protective earplug comprising: a soft, resilient, polymeric foam body comprising a smoothly contoured viscoelastic main body element having a rounded nose end, and a maximum cross sectional dimension along its length of about 13.73 mm, said foam body comprising a base end opposite said nose end of said main body element;

an elongate stem having two ends, one end thereof being embedded in and secured to the interior of the nose end portion of said main body element, said stem extending axially and rearwardly from said nose end portion and through said base end, the other end of said stem terminating at a point exterior said base end, said stem being sufficiently stiff as to allow manipulation of said main body element into an ear canal whether in a precompressed or uncompressed condition;

said viscoelastic main body element of said earplug having a 90% recovery rate of between 2 and 120 seconds and is capable of being inserted into an ear canal in either a precompressed or uncompressed condition.

2. The earplug of claim 1 wherein said main body element has a 90% recovery rate of between 10 and 60 seconds.

3. The earplug of claim 1 wherein the apparent density of said main body element is no greater than about 0.32 g/cm$^3$.

4. The earplug of claim 1 wherein the apparent density of said main body element is no greater than about 0.24 g/cm$^3$.

5. The earplug of claim 1 wherein the exterior shape of said main body element is hemispherical and the length to diameter ratio thereof is about 0.5 to 1.

6. The earplug of claim 1 wherein the exterior shape of said main body element is bullet shaped.

7. The earplug of claim 1 wherein said foam body is composed of a polyurethane.

8. The earplug of claim 7 wherein said polyurethane is a polyether polyurethane.

9. The earplug of claim 7 wherein said foam body is composed of a polyether polyurethane containing an acrylic latex modifier.

10. The earplug of claim 7 wherein said polyurethane foam precursor formulation contains an acrylic latex modifier.

11. The earplug of claim 1 wherein the maximum cross sectional dimension of that portion of said stem element embedded in said main body element is between about 3.2 mm and about 4.0 mm.

12. The earplug of claim 1 wherein said main body element has an outboard end which transitions into a terminal flared end portion having a maximum cross sectional dimension which is larger than the external auditory meatus of the average human ear canal, whereby said terminal flared end portion functions as a stop means upon insertion of the earplug into the ear canal.

13. The earplug of claim 12 wherein said terminal flared end portion is of circular cross section and has a diameter of about 13.73 mm to about 19.05 mm.

14. The earplug of claim 1 wherein said main body element is of circular cross section.

15. The earplug of claim 1 wherein said main body element has a circular cross section.

16. The earplug of claim 1 wherein said main body element has an ovoid cross section.

* * * * *